US010179233B2

(12) United States Patent
Vardiman

(10) Patent No.: US 10,179,233 B2
(45) Date of Patent: Jan. 15, 2019

(54) IMPLANTABLE LEAD PROTECTOR

(71) Applicant: Arnold B. Vardiman, San Antonio, TX (US)

(72) Inventor: Arnold B. Vardiman, San Antonio, TX (US)

( * ) Notice: Subject to any disclaimer, the term of this patent is extended or adjusted under 35 U.S.C. 154(b) by 0 days.

(21) Appl. No.: 15/256,528

(22) Filed: Sep. 3, 2016

(65) Prior Publication Data

US 2018/0064928 A1 Mar. 8, 2018

(51) Int. Cl.
*A61N 1/05* (2006.01)

(52) U.S. Cl.
CPC .................................. *A61N 1/0534* (2013.01)

(58) Field of Classification Search
CPC ............................ A61N 1/0534; A61N 1/0565
See application file for complete search history.

(56) References Cited

U.S. PATENT DOCUMENTS

2005/0004637 A1* 1/2005 Singhal .................. A61N 1/375 607/116
2005/0107753 A1* 5/2005 Rezai ................ A61M 5/14276 604/288.04
2008/0058876 A1* 3/2008 Barolat .................. A61N 1/375 607/3
2016/0250466 A1* 9/2016 Boggs, II ........... A61N 1/36021 607/46

* cited by examiner

*Primary Examiner* — Rex R Holmes
(74) *Attorney, Agent, or Firm* — Whittaker Law Firm; Malcolm E. Whittaker

(57) ABSTRACT

An implantable lead protector, comprising, an upper surface; a lower surface; a spool disposed between the upper surface and the lower surface; and, a protective channel disposed at least partially therethrough the spool, the protective channel further comprising a curved outer wall and a curved inner wall; whereby a least a portion of a lead can be slidably received into the protective channel and at least a portion of the lead may be wound around the spool.

20 Claims, 21 Drawing Sheets

IMPLANTABLE LEAD PROTECTOR

CROSS-REFERENCE TO RELATED APPLICATIONS

None

STATEMENT REGARDING FEDERALLY SPONSORED RESEARCH

Not Applicable.

TECHNICAL FIELD OF THE INVENTION

The technical field of the invention relates to an electrical lead protector.

The technical field of the invention relates to an electrical lead protector used in conjunction with use of electrical stimulation to alleviate pain.

The technical field of the invention relates to an electrical lead protector for use in conjunction with a cardiac pacemaker.

The technical field of the invention relates to deep brain stimulating probes.

The present invention relates to an electrical lead protector for a deep brain system with a mono-lead.

The present invention related to an electrical lead protector for a mono-lead implanted electrode or stimulator.

The present invention relates to an electrical protector for a deep brain system with two leads. This may also be referred to as a bi-lead deep brain stimulator. This may also be referred to as a two-lead deep brain stimulator.

The present invention relates to an electrical protector for a deep brain system with two or more leads. This may also be referred to as a deep brain stimulator with a plurality of leads.

BACKGROUND OF THE INVENTION

A variety of disabling diseases affecting the central nervous system have proven responsive to treatment using electrical stimulation of specific anatomic targets within the human brain, neural tissue, cardiac tissue, spine, limbs, torso, peripheral nerves, cranial nerves and other regions and parts of the body. Examples of disabling diseases affecting the central nervous system are Parkinson's disease, multiple sclerosis, pain, seizure disorders, psychiatric disorders such as depression, obsessive compulsive disorder (OCD) and the like.

At the present time, devices designed to produce deep brain stimulation use a standard set of components including a pulse generator, an extension kit, and an electrode. The pulse generator is electrically connected to the electrode and the electrode is surgically implanted within a patient's body. Typically, the extension kit is an intermediate connector between the pulse generator and the electrode. The pulse generator can produce a modulatable electrical field/current. At the present time, the electrode has four electrode contacts arranged as narrowly spaced bands on the terminal end of a stimulating electrode. This may also be referred to as a lead with electrodes disposed thereon.

It has also been found that electrical stimulation can be used in a various locations in the human body. For example, pacemakers can provide electrical stimulation to a patient's heart.

Examples of situations affecting the heart and circulatory system that may potentially be treatable with electrical stimulation include: bradyarrhtymia; this condition may require electrical stimulation, also known as pacing; tachycardia, including ventricular flutter and ventricular fibrillation where the characteristic waveforms of the electrical activity of the patient's heart are irregular and potentially chaotic. In this situation, a defibrillator is used to depolarize the heart muscle and terminate the dysrhythmia and allow the patient's body to reestablish a normal sinus rhythm.

Similarly, providing an electrical current to reduce or eliminate pain by effectively modulating the activity of the body's pain receptors can mitigate pain. The pain receptors transmit pain messages from the pain receptors to the brain. In other words, if the pain receptors' pain messages are effectively interdicted or mitigated, then the brain is unaware of the pain and the patient does not feel the pain.

In each of these situations, energy is conveyed from an energy source, typically a battery, to an electrode. The electrical line, generally referred to as a lead, conveys the stored energy in the battery to electrodes proximate the portion of the body where electrical stimulation can be beneficial. In many situations, the battery, the lead and the electrodes are implanted. It has been found that the lead is vulnerable to damage during implant, use, and removal or revision.

SUMMARY OF THE INVENTION

An implantable lead protector, comprising, an upper surface; a lower surface; a spool disposed between the upper surface and the lower surface; and, a protective channel disposed at least partially therethrough the spool, the protective channel further comprising a curved outer wall and a curved inner wall; whereby a least a portion of a lead can be slidably received into the protective channel and at least a portion of the lead may be wound around the spool.

An implantable bi-lead protector, comprising, an upper surface; a lower surface; an intermediate surface disposed between the upper surface and the lower surface; an upper spool disposed between the upper surface and the intermediate surface; an lower spool disposed between the intermediate surface and the lower surface; and, an upper protective channel disposed at least partially therethrough the upper spool, the upper protective channel further comprising a curved outer wall and a curved inner wall; a lower protective channel disposed at least partially therethrough the lower spool, the protective channel further comprising a curved outer wall and a curved inner wall; whereby the upper protective channel can slidably receive one of the leads and the lower protective channel can slidably receive the other lead and at least a portion of the one of the leads may be wound around one spool and at least a portion of the other lead may be wound around the other spool.

These and other embodiments will be more fully appreciated from the description below.

BRIEF DESCRIPTION OF THE DRAWINGS

FIG. 1C illustrates a plan view of the current state of the technology, i.e. prior art, illustrating a prior art deep brain stimulator system implanted in a patient's brain.

DESCRIPTION OF THE PREFERRED EMBODIMENTS

Corresponding reference numbers indicate corresponding parts throughout the several views of the drawings and specification.

Figure 1A:
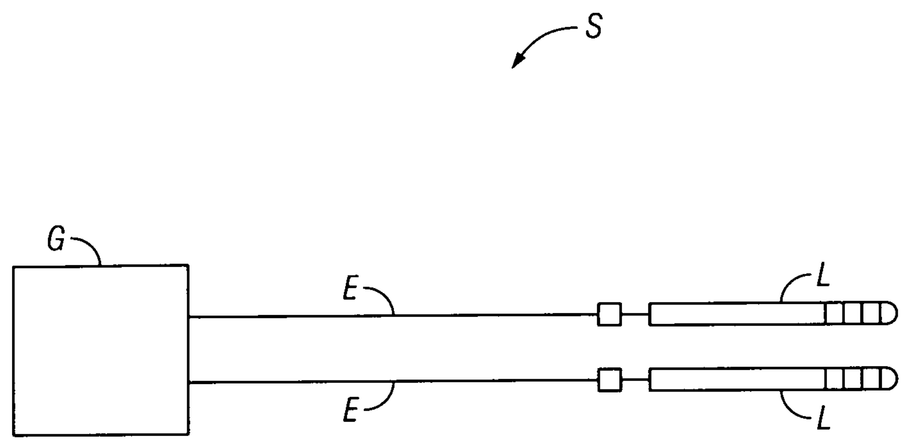
FIG. 1A illustrates a plan view of a prior art deep brain stimulating system.
Figure 1B:
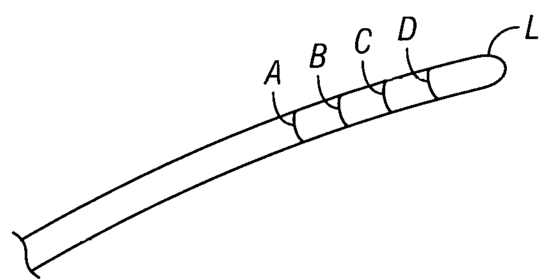
FIG. 1B illustrates a partial plan view of a prior art deep brain stimulator lead.
Figure 1C:
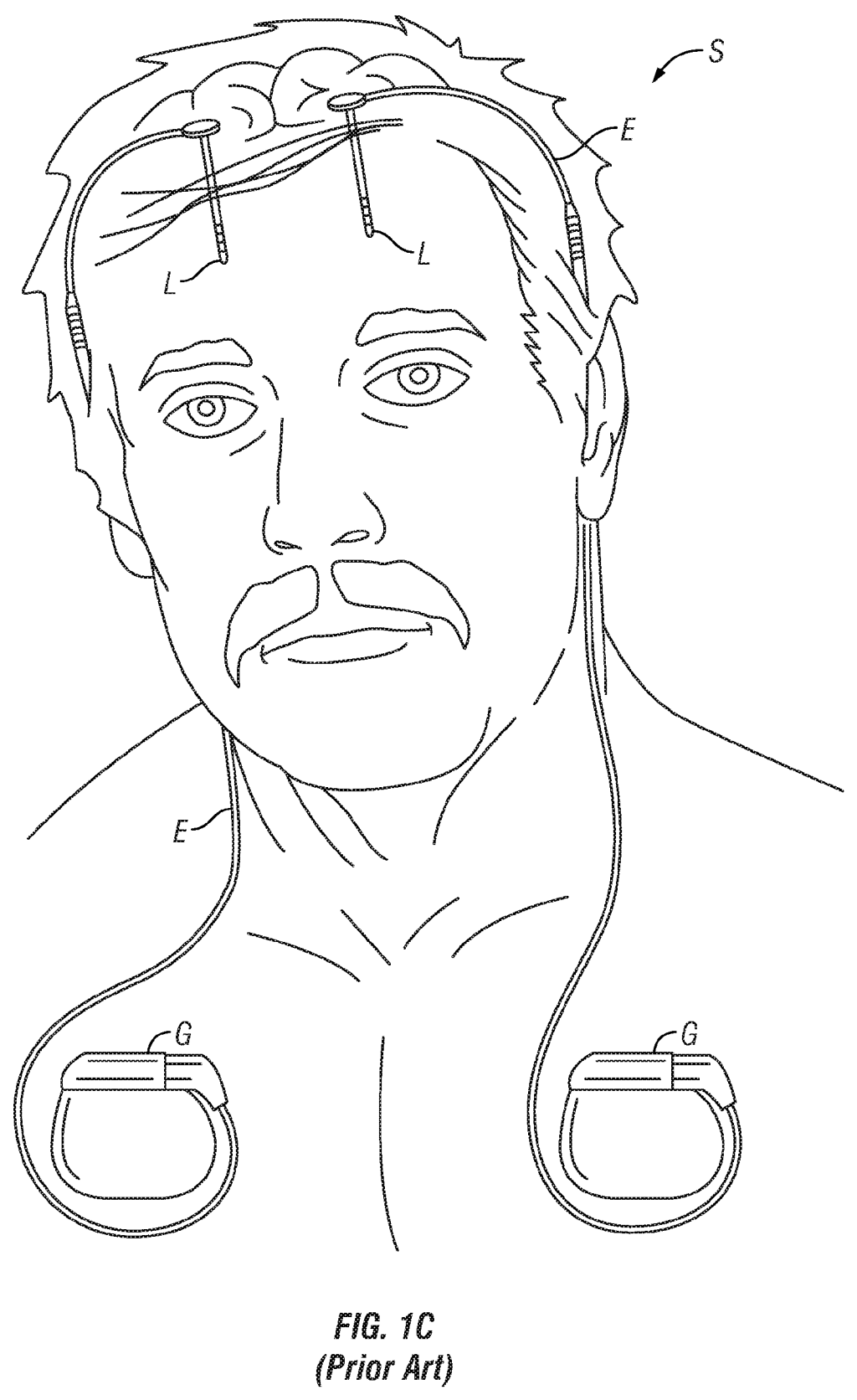

As illustrated in FIGS. 1A, 1B, and 1C, deep brain stimulation (DBS) is a surgical therapy, which broadly speaking, involves implanting one or more deep brain stimulator systems S into a specific area of a patient's body. Deep brain stimulator S further comprises a pulse generator G, an extension kit E and at least one lead L. Electrical lead L is electrically connected, by extension kit E, to a neurostimulator, also referred to as a pulse generator G.

The three main parts of the brain where the DBS lead L may be placed to provide therapy for Parkinson's disease, essential tremor and dystonia are the globus pallidus internus, the thalamus, and the subthalamic nucleus. The DBS lead L is connected to a pacemaker-like device that is implanted in the chest region below the collarbone. This device, called the neurostimulator or implantable pulse generator G, contains the battery and computer source that generates the electrical pulses that will be delivered via the lead L to the brain. The system can be turned on or off by the patient or the clinician. In addition, the clinician can select which one or more of the four electrodes on each lead that are to be activated to provide electrical stimulation. This process allows electrical stimulation to be delivered to a very precise part of the brain.

Similarly, an electrical stimulator G, extension kit E, and lead L may be used to provide an electrical or magnetic field to stimulate cardiac tissue. For example, pacemaker pulse generators, defibrillators or other cardiac implantable electronic devices (CIED) Lead L may also be used to generate an electrical or magnetic field to alleviate pain. As such, lead L may be implanted in the body such that the electrical field generated by an electrode of lead L can alleviate pain or even neurological illnesses or psychiatric symptoms.

FIG. 1A illustrates a currently available deep brain stimulation system comprising a pulse generator G, an extension kit E and leads L. As illustrated in FIG. 1B, lead L further comprises four electrodes (A, B, C and D) arranged as narrowly spaced bands on the terminal end, also referred to as the distal end, (i.e. the end of lead L that is implanted into the brain or other tissue) of lead L. The physiologic effect of the stimulation of electrodes (A, B, C or D) can be modulated by altering which electrode (A, B, C or D) is energized or by altering the amplitude, frequency or pulse width of the electrical current. The shape of the stimulating electrical or magnetic field can also be modified to ensure that the electrical or magnetic field and the targeted treatment zone in the body coincide. At the present time, the four banded, also referred to as cylindrical or circumferential, electrodes (A, B, C, or D) seen in FIGS. 1A, 1B and 1C are fixed in position on lead L.

FIG. 1B illustrates lead L. As discussed above, lead L further comprises four banded electrodes (A, B, C, and D) disposed on the distal end of lead L, i.e. the end of lead L that is implanted into the patient's brain to provide therapy. FIG. 1B also illustrates that lead L has a distal end and a proximal end. As noted above, four-banded electrodes are disposed in the distal end D of lead L. Typically, lead L is on the order of 40 centimeters in length and is on the order of about 1.27 millimeters to about 1.47 millimeters in diameter. Broadly speaking, lead L is a thin insulated wire. Conventional examples of prior art deep brain-stimulating (DBS) leads are Medtronic's lead models 3387 and 3389. Medtronic leads 3387 and 3389 have an internal section made of platinum-iridium. Similarly, the four-banded electrodes are also made of platinum-iridium. Lead L is insulated with a thin layer of polyurethane or a similar material. Preferably, because they are implanted in vivo in the brain, these materials should be biocompatible.

FIG. 1C illustrates deep brain stimulator S implanted in a patient. As illustrated in FIG. 1C, two leads L may be implanted in hemispheres of a patient's brain or a single lead L may be implanted in one hemisphere of the patient's brain. Thus, brain stimulator S may have one lead L implanted in each hemisphere of a patient's brain as illustrated in FIG. 1C. Use of a single lead may also be referred to as unilateral placement of lead L. This may also be referred to as a mono-lead deep brain stimulator or a single lead deep brain stimulator. Insertion of two leads L into the brain may also be referred to as a bilateral placement of lead L. This may also be referred to as a bi-lead deep brain stimulator or a dual-lead deep brain stimulator or a two-lead deep brain stimulator.

As illustrated in FIGS. 1A, 1B and 1C, leads L and extension kit lines E are typically a standard size. Because patients are not all exactly the same size, extension kit E may be longer than is required to interconnect lead L with pulse generator G. Phrased differently, current surgical practice is to coil lead L and retain it beneath the patient's skin. This type of placement of lead L may result in a bent or damaged lead. Vulnerability of the lead L in this situation is amplified by the fact that the coiling process is haphazard and may lead to sharp kinks and stress points particularly at distal contact points of the lead L. Since most procedures to implant lead L are staged with a second procedure to retrieve and connect lead L to extension kit E and pulse generator G, lead L is also vulnerable to damage during explant and dissection.

Figure 2A:
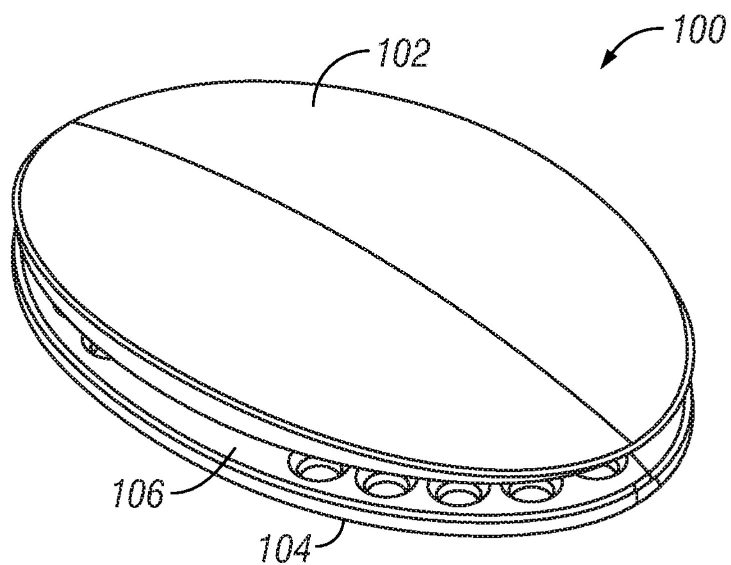
FIG. 2A illustrates a perspective view of a mono-lead electrical lead protector.

FIG. 2A illustrates a mono-lead electrical lead protector 100. Mono-lead protector 100 further comprises top surface 102, bottom surface 104 and spool 106.

Figure 2B:
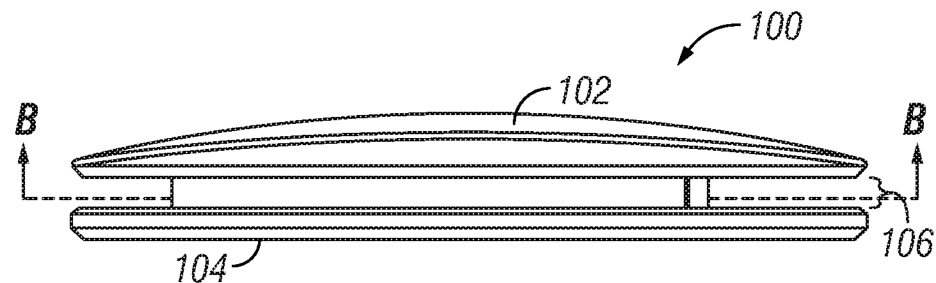
FIG. 2B illustrates a front plan view of the mono-lead electrical lead protector of FIG. 2A.

FIG. 2B illustrates mono-lead electrical lead protector 100 and also illustrates top surface 102.

Figure 2C:
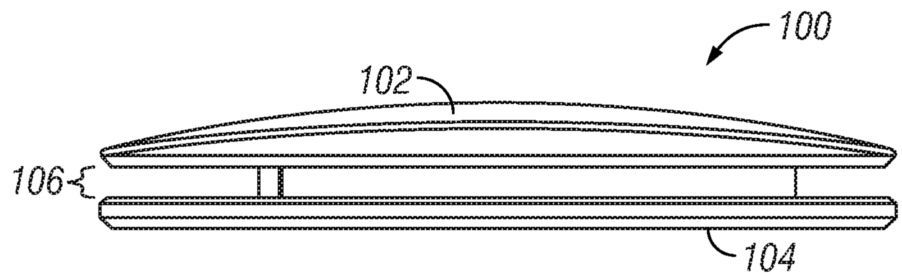
FIG. 2C illustrates a rear plan view of the mono-lead electrical lead protector of FIGS. 2A and 2B.

FIG. 2C illustrates a rear view of the mono-lead electrical lead protector 100 and also illustrates top surface 102, bottom surface 104 and spool 106.

Figure 2D:
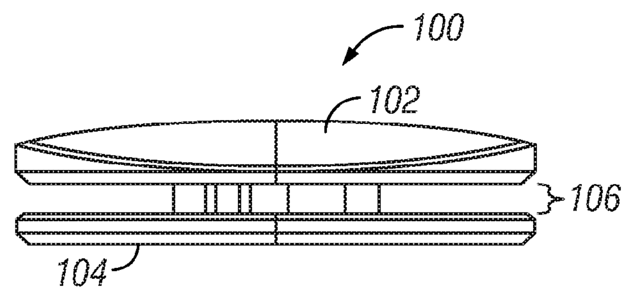
FIG. 2D illustrates a left side plan view of the mono-lead electrical lead protector of FIGS. 2A, 2B and 2C.

FIG. 2D illustrates a right side view of mono-lead electrical lead protector 100 and also illustrates top surface 102, bottom surface 104 and spool 106.

Figure 2E:
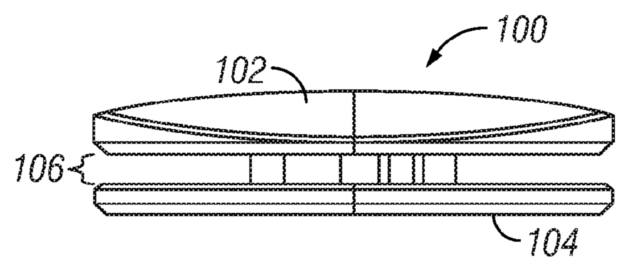
FIG. 2E illustrates a right side plan view of the mono-lead electrical lead protector of FIGS. 2A, 2B, 2C and 2D.

FIG. 2E illustrates a right side view of mono-lead electrical lead protector 100 and also illustrates top surface 102, bottom surface 104 and spool 106.

Figure 2F:
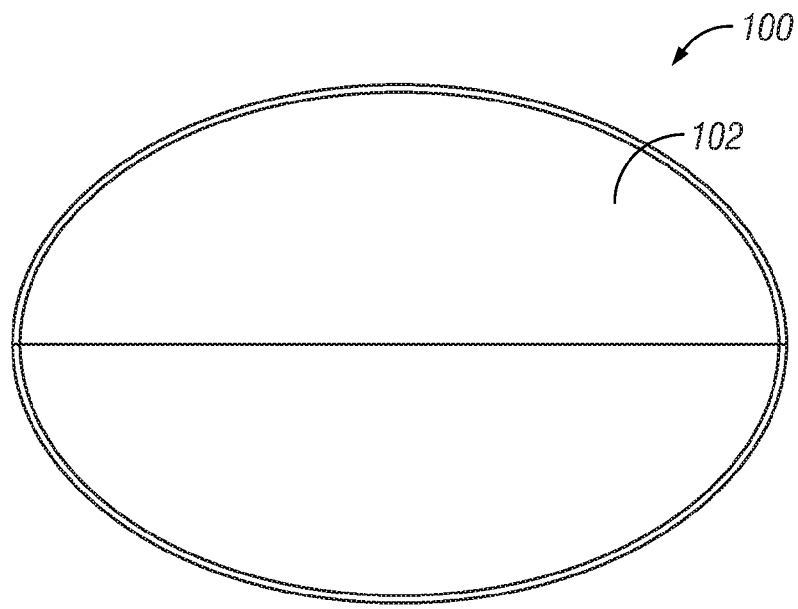
FIG. 2F illustrates a top plan view of the mono-lead electrical lead protector of FIGS. 2A, 2B, 2C, 2D and 2E.

FIG. 2F illustrates a top view of mono-lead electrical lead protector 100 and also illustrates top surface 102.

Figure 2G:
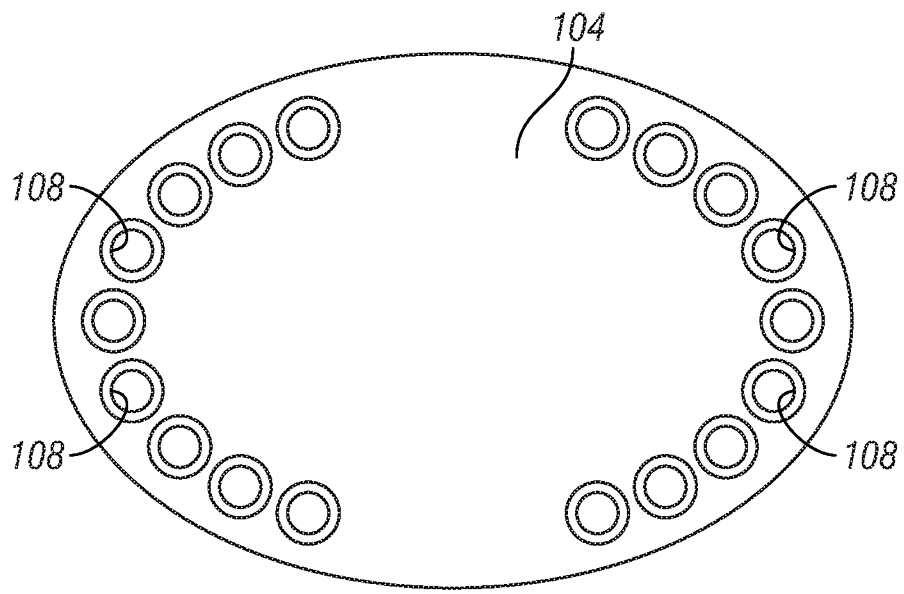
FIG. 2G illustrates a bottom plan view of the mono-lead electrical lead protector of FIGS. 2A, 2B, 2C, 2D, 2E and 2F.

FIG. 2G is a bottom view of view of mono-lead electrical lead protector 100 and illustrates bottom surface 102. Bottom surface 104 further comprises attachments loops 108.

Figure 2H:
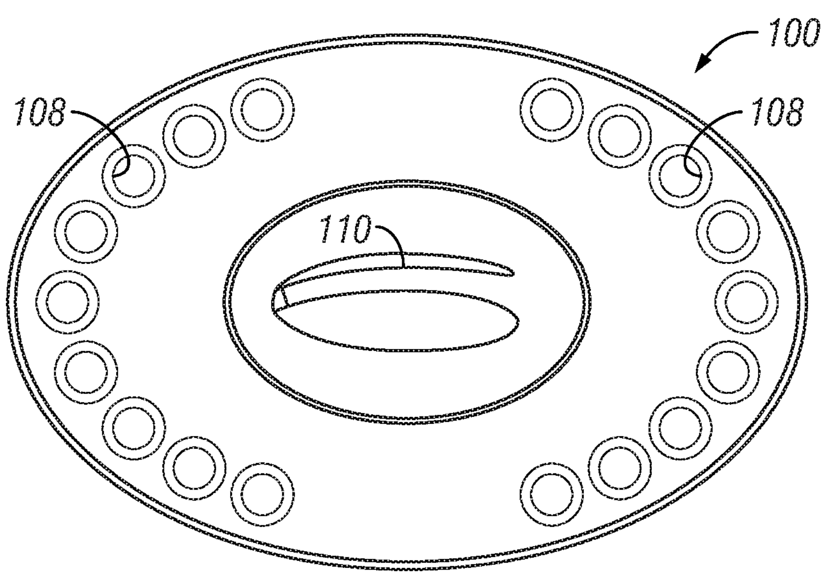
FIG. 2H illustrates a cross-sectional top view of the mono-lead electrical protector taken along the line B-B.
Figure 2I:
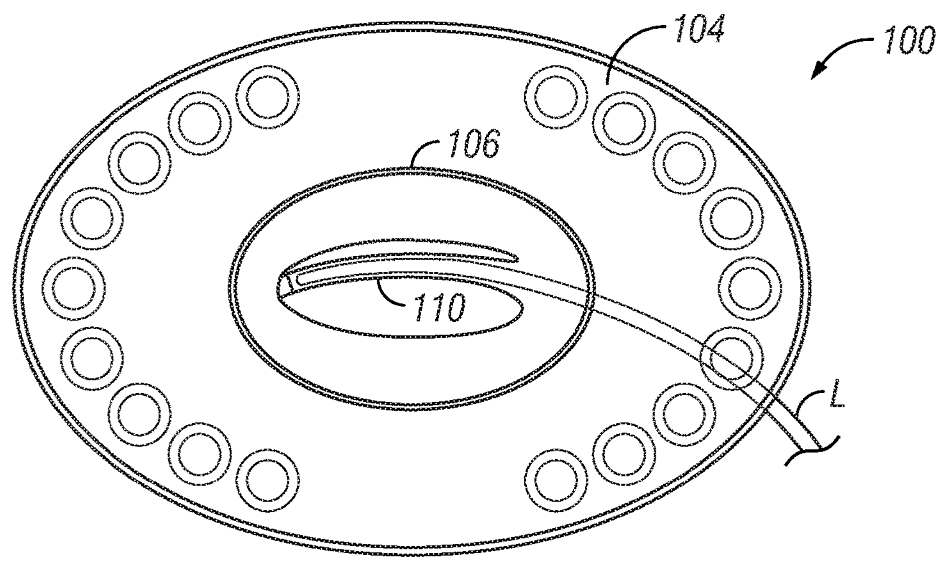
FIG. 2I illustrates a top view of the mono-lead electrical protector of FIG. 2H illustrating a lead being retained in the protective channel of the mono-lead electrical protector.

FIG. 2H illustrates a cross-sectional view of FIG. 2B and shows a protective channel 110. Protective channel 110 receives one end of lead L and thereby stores and retains lead L. As illustrated in FIGS. 2H and 2I, lead L is semi-rigid and generally retains its shape when inserted into protective channel 110. As discussed above, the diameter of lead L is on the order of 1.27 mm. The proximal end P of lead L is inserted into protective channel 110. Preferably, channel 110, and all of lead protector 100, should be formed of a resilient deformable material that can receive and retain the proximal end of lead L. Preferably, channel 110 should be no more than 1.0 mm wide. In this way, lead L is removably retained within channel 110. This may be thought of as a pressure fit or an interference fit that occurs when the exterior surface of lead L and channel 110 are slightly plastically deformed when lead L is inserted therein. The result is that both parts elastically deform slightly creating a frictional force that retains lead L within channel 110. This may be thought of as holding lead L within channel 110. It has been found that if lead L is 1.27 mm that it will be removably retained when channel 110 is on the order of 1.0 mm. Thus, channel 110 does not permanently retain lead L. Experiments with channel 110 indicate that an inner radius of 1.446 inches [3.672 centimeters] and an outer radius of 1.784 inches [4.531 centimeters] are preferred. Phrased differently, the inner and outer radiuses of channel 110 are not identical. This also means that the radiuses of curvature of the inner and outer radius of protective channel 110 are not the same. In other words, in the preferred embodiment, the inner wall has a radius on the order of about 1.446 inches [3.672 centimeters] and the outer wall has a radius of about 1.784 inches [4.531 centimeters].

Figure 2J:
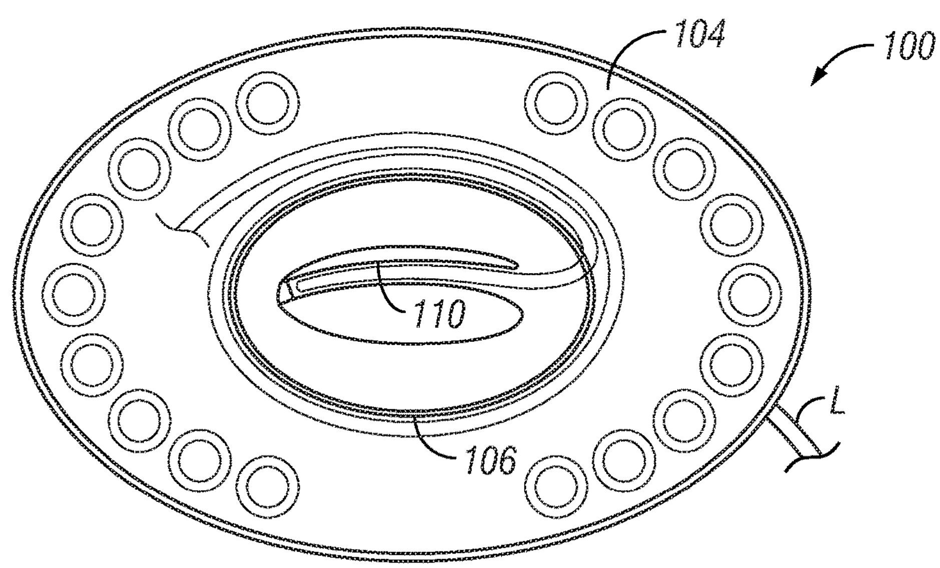
FIG. 2J illustrates a top of the mono-lead electrical protector of FIG. 2I illustrating the lead being coilingly retained (i.e. wound around the spool) within the mono-lead electrical protector.

FIGS. 2I and 2J illustrate that channel 110 removably retains the unimplanted end of lead L after lead L has been implanted into the patient's brain.

Figure 3A:
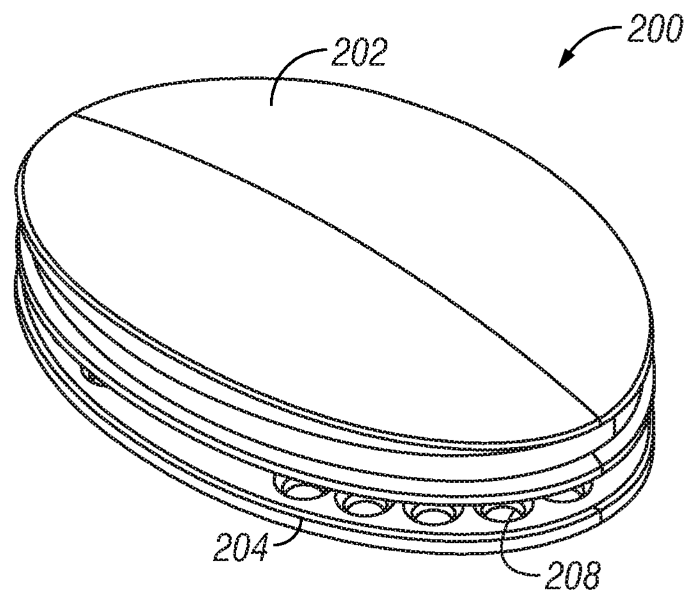
FIG. 3A illustrates a perspective view of a bi-lead electrical lead protector.

FIG. 3A illustrates a perspective view of a bi-lead electrical lead protector 200. Bi-lead electrical protector 200 further comprises top surface 202, bottom surface 204, spool 206 and attachment loops 208.

Figure 3B:
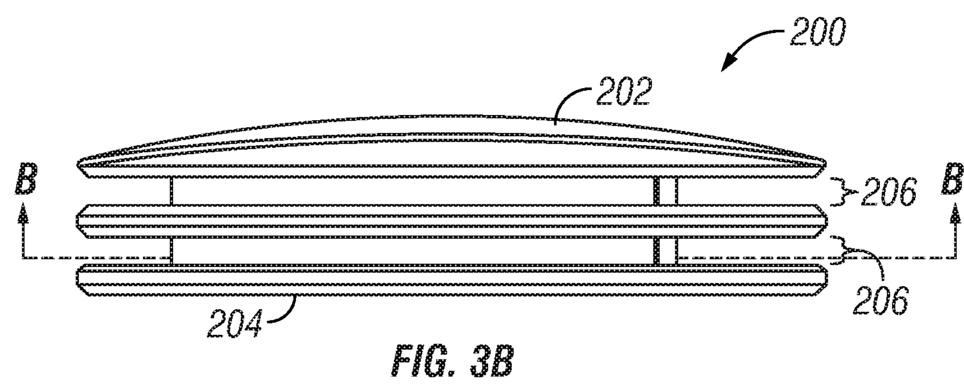
FIG. 3B illustrates a front plan view of the bi-lead electrical lead protector of FIG. 3A.

FIG. 3B is a front view of the bi-lead electrical lead protector 200 of FIG. 3A. Bi-lead electrical protector 200 further comprises top surface 202, bottom surface 204, spools 206 and attachment loops 208.

Figure 3C:
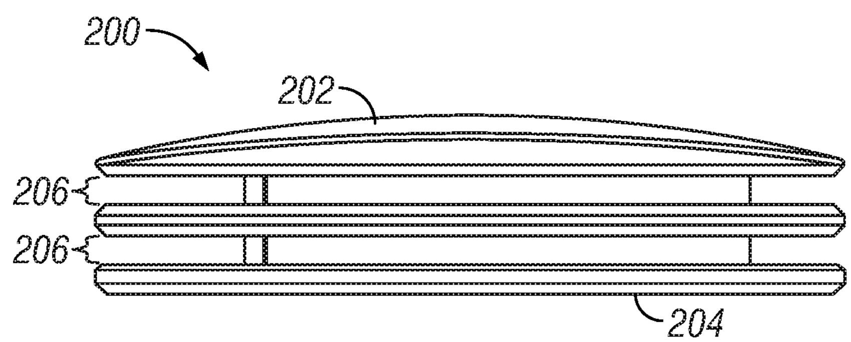
FIG. 3C illustrates a back plan view of the bi-lead electrical lead protector of FIGS. 3A and 3B.

FIG. 3C is a back view of the bi-lead electrical lead protector 200 of FIGS. 3A and 3B. As discussed above, bi-lead electrical protector 200 further comprises top surface 202, bottom surface 204, spools 206 and attachment loops 208.

Figure 3D:
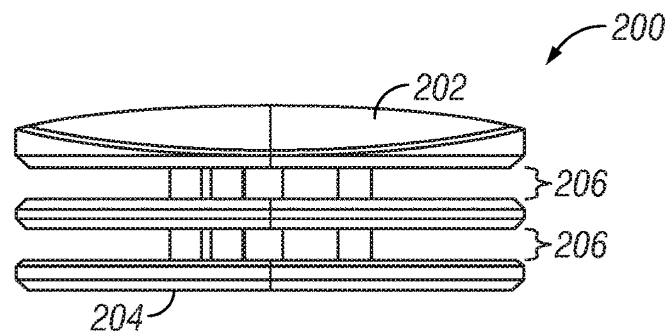
FIG. 3D illustrates a left side plan view of the bi-lead electrical lead protector of FIGS. 3A, 3B and 3C.

FIG. 3D is a left side view of the bi-lead electrical lead protector of FIGS. 3A, 3B and 3C and illustrates that bi-lead electrical protector 200 further comprises top surface 202, bottom surface 204, spools 206 and attachment loops 208.

Figure 3E:
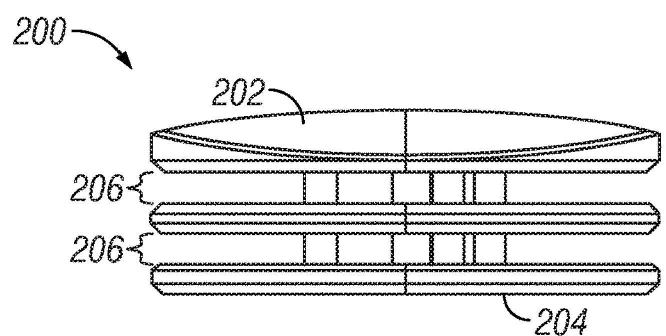
FIG. 3E illustrates a right side plan view of the bi-lead electrical lead protector of FIGS. 3A, 3B, 3C and 3D.

FIG. 3E is a right side view of the bi-lead electrical lead protector of FIGS. 3A, 3B, 3C and 3D.

Figure 3F:
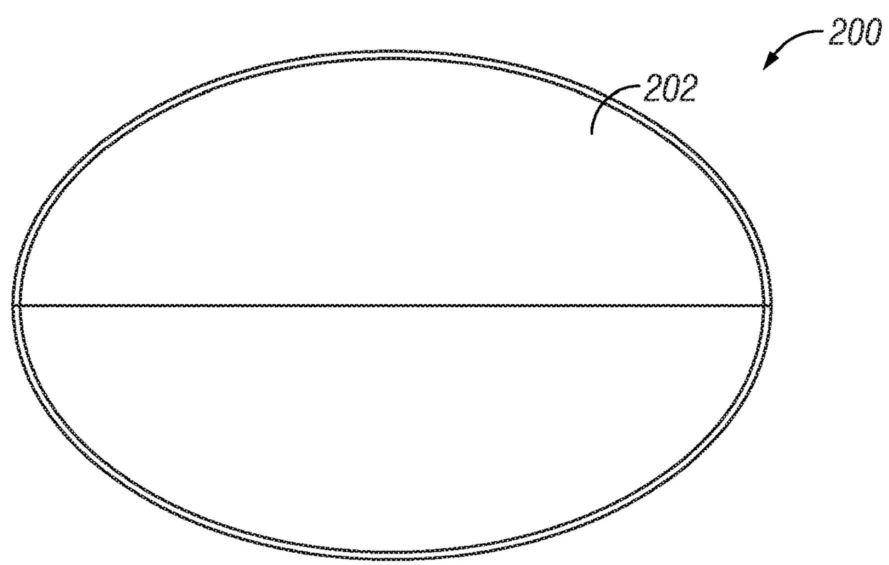
FIG. 3F illustrates a top plan view of the bi-lead electrical lead protector of FIGS. 3A, 3B, 3C, 3D and 3E.

FIG. 3F is a top view of the bi-lead electrical lead protector of FIGS. 3A, 3B, 3C, 3D and 3E.

Figure 3G:
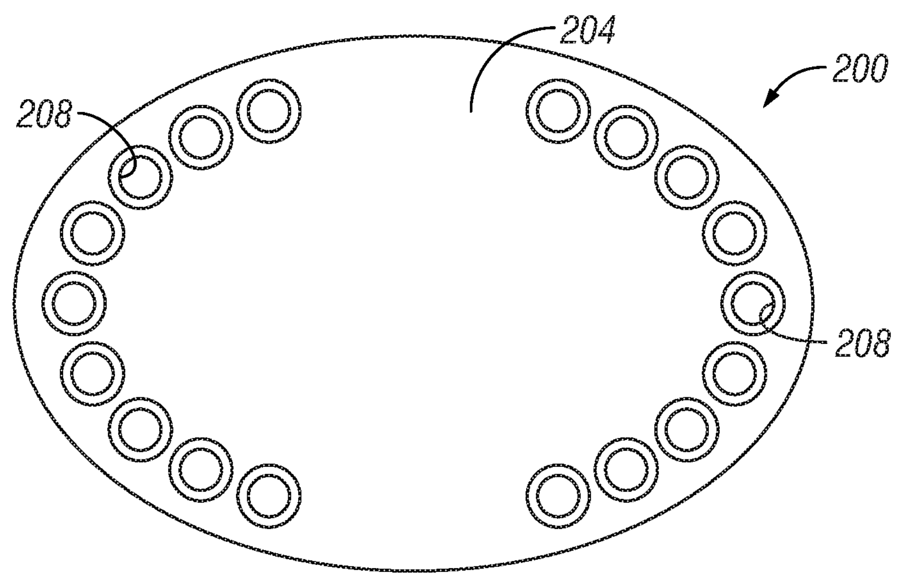
FIG. 3G illustrates a bottom plan view of the bi-lead electrical lead protector of FIGS. 3A, 3B, 3C, 3D, 3E and 3F.

FIG. 3G is a bottom view of the bi-lead electrical lead protector of FIGS. 3A, 3B, 3C, 3D, 3E and 3F.

Figure 3H:
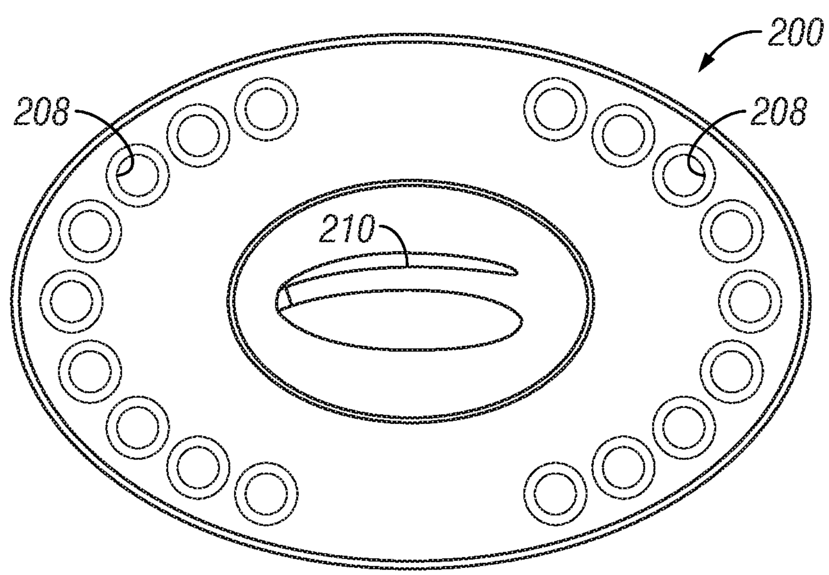
FIG. 3H illustrates a cross-sectional top view of the bi-lead electrical protector taken along the line B-B.
Figure 3I:
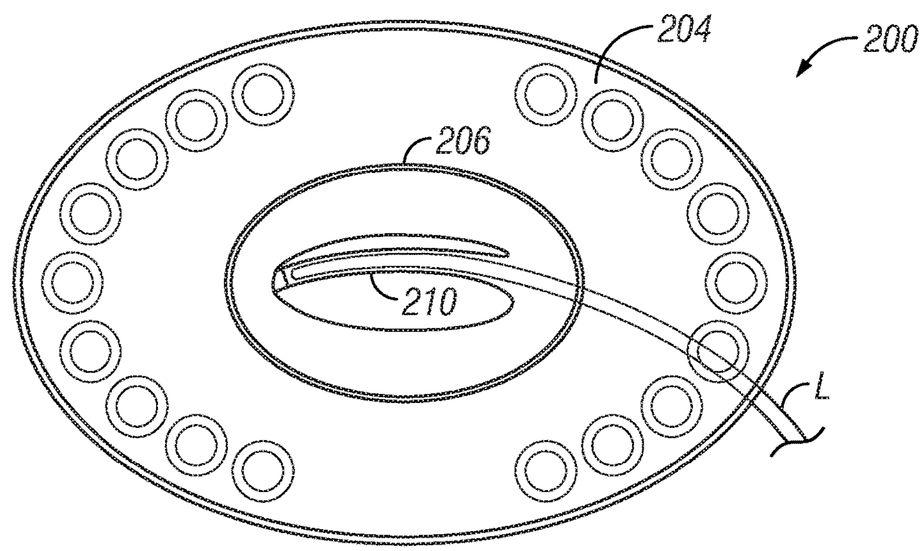
FIG. 3I illustrates a cross-sectional top view of the bi-lead electrical protector of FIG. 3H illustrating a lead being retained in the protective channel of the bi-lead electrical protector.

FIG. 3H is a cross-section top view of the mono-lead electrical protector 200 taken along the line B-B and illustrates a protective channel 210. Protective channel 210 receives the proximal end P of lead L and thereby stores and removably retains the proximal end of lead L. As illustrated in FIGS. 3H and 3I, lead L is semi-rigid and generally retains its shape when inserted into protective channel 210. As discussed above, the diameter of lead L is on the order of 1.27 mm. The proximal end of lead L is inserted into protective channel 210. Preferably, channel 210, and all of lead protector 200, should be formed of a resilient deformable material that can receive and retain the proximal end of lead L. Preferably, channel 210 should be no more than 1.0 mm wide. In this way, lead L is removably retained within channel 210. This may be thought of as a pressure fit or an interference fit that occurs when the exterior surface of lead L and channel 210 are slightly plastically deformed. The result is that both parts elastically deform slightly creating a frictional force that retains lead L within channel 210. This may be thought of as holding lead L within channel 210. It has been found that if lead L is 1.27 mm that it will be removably retained when channel 210 is on the order of 1.0 mm. Channel 210 does not permanently retain lead L. Experiments with channel 210 indicate that an inner radius of 1.446 inches [3.672 centimeters] and an outer radius of 1.784 inches [4.531 centimeters] are preferred. Phrased differently, the inner and outer radiuses of channel 210 are not identical. This also means that the radiuses of curvature of the inner and outer radius are not the same. This also means that the radiuses of curvature of the inner and outer radius are not the same. In other words, the inner wall has a radius on the order of about 1.446 inches [3.672 centimeters] and the outer wall has a radius of about 1.784 inches [4.531 centimeters].

Figure 3J:
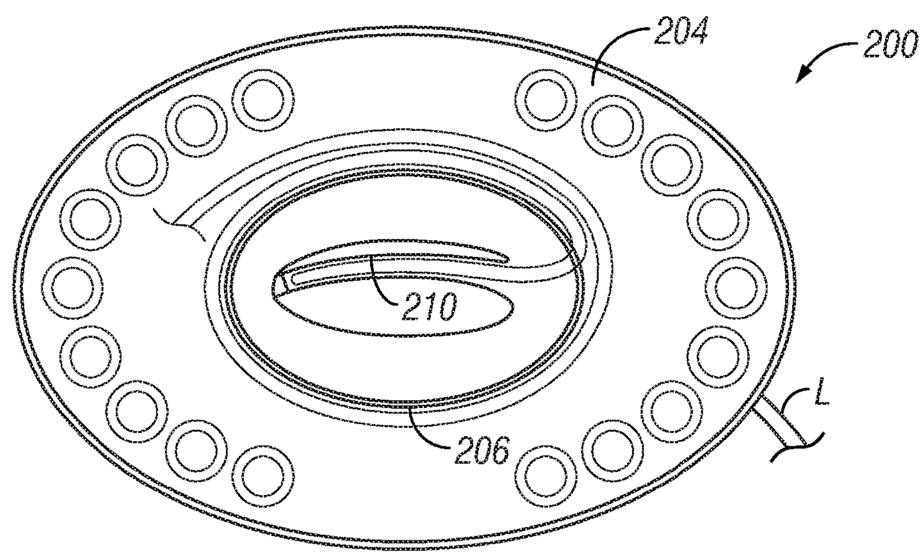
FIG. 3J illustrates a top view of the bi-lead electrical protector of FIG. 3I illustrating a lead being retained in one of the retaining channels of the protective channel of the mono-lead electrical protector and illustrating the lead being coilingly retained (i.e. wound around the spool) within the bi-lead electrical protector.

FIGS. 3I and 3J illustrate channel 210 removably retaining the unimplanted end of lead L after lead L has been implanted into the patient's brain.

Figure 4A:
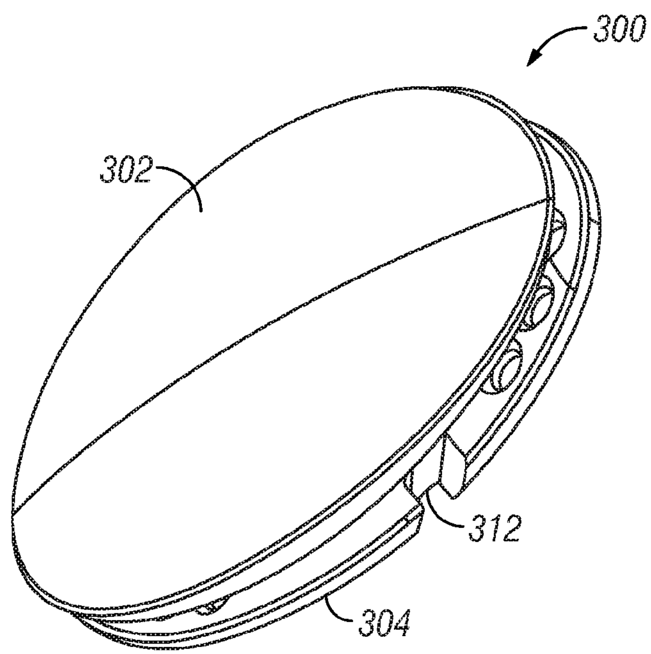
FIG. 4A illustrates a perspective view of an alternative embodiment of a mono-lead electrical lead protector further comprising a retaining groove.

FIG. 4A illustrates a perspective view of an alternative embodiment of a mono-lead electrical lead protector 300.

Figure 4B:
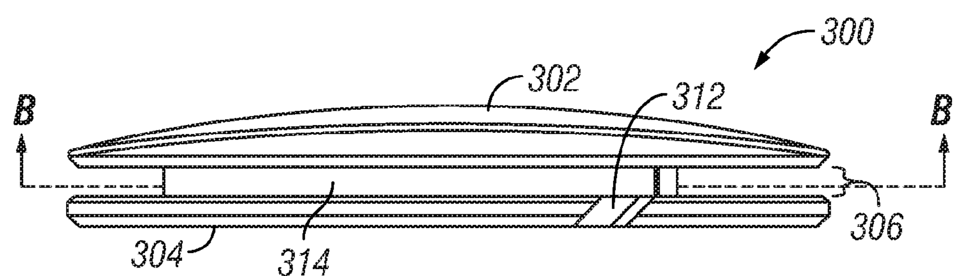
FIG. 4B illustrates a front plan view of the alternative embodiment of the mono-lead electrical lead protector of FIG. 4A.

FIG. 4B illustrates a front view of an alternative embodiment the mono-lead electrical lead protector 300 of FIG. 4A. FIG. 4B also illustrates top surface 302, bottom surface 304, spool 306, attachment loops 308, protective channel 310, and retaining grooves 312.

Figure 4C:
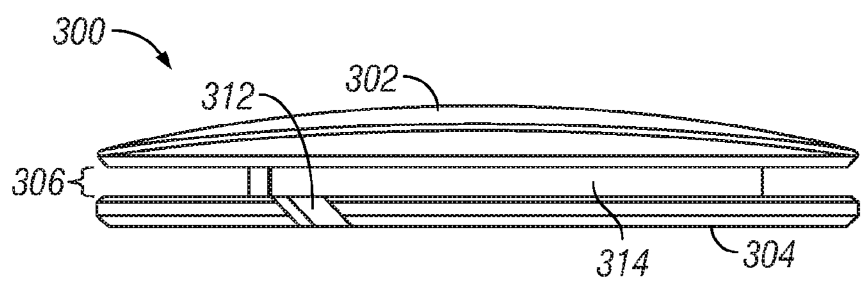
FIG. 4C illustrates a back plan view of the alternative embodiment of the mono-lead electrical lead protector of FIGS. 4A and 4B.

FIG. 4C illustrates a back view of an alternative embodiment the mono-lead electrical lead protector 300 of FIGS. 4A and 4B.

Figure 4D:
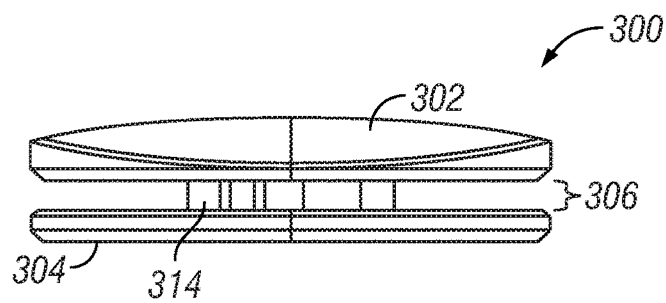
FIG. 4D illustrates a left side plan view of the alternative embodiment of the mono-lead electrical lead protector of FIGS. 4A, 4B and 4C.

FIG. 4D illustrates a left side view of an alternative embodiment of the mono-lead electrical lead protector 300 of FIGS. 4A, 4B and 4C.

Figure 4E:
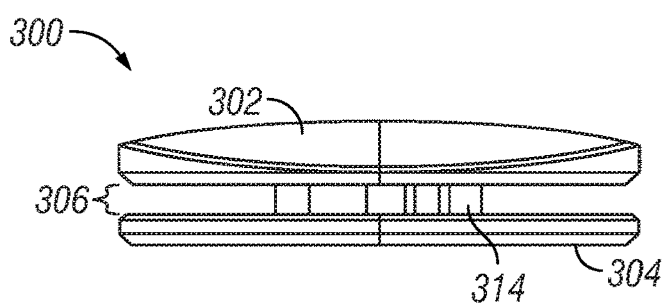
FIG. 4E illustrates a right side plan view of the alternative embodiment of the mono-lead electrical lead protector of FIGS. 4A, 4B, 4C and 4D.

FIG. 4E illustrates a right side view of an alternative embodiment of the mono-lead electrical lead protector 300 of FIGS. 4A, 4B, 4C and 4D.

Figure 4F:
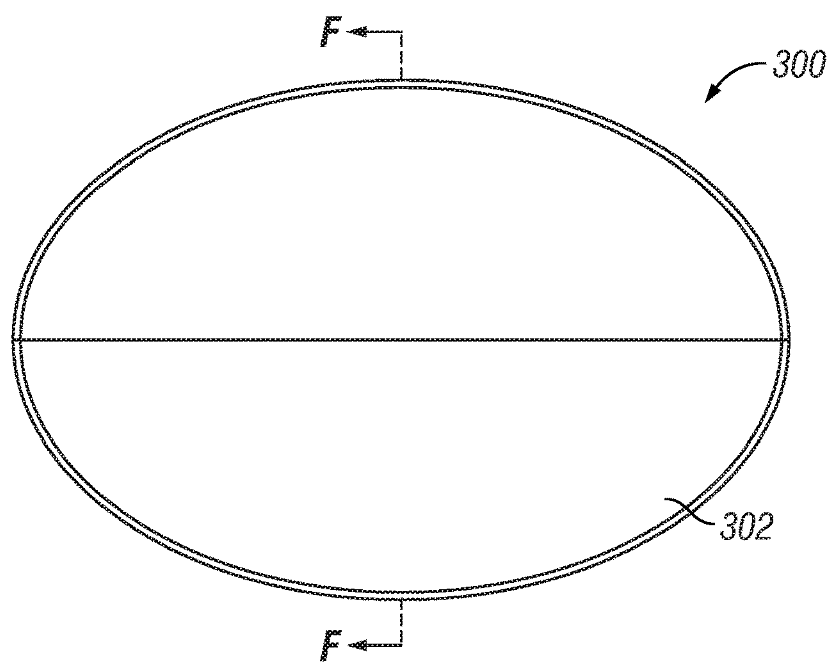
FIG. 4F illustrates a top plan view of the alternative embodiment of the mono-lead electrical lead protector of FIGS. 4A, 4B, 4C, 4D and 4E.

FIG. 4F illustrates a top view of an alternative embodiment of the mono-lead electrical lead protector 300 of FIGS. 4A, 4B, 4C, 4D and 4E.

Figure 4G:
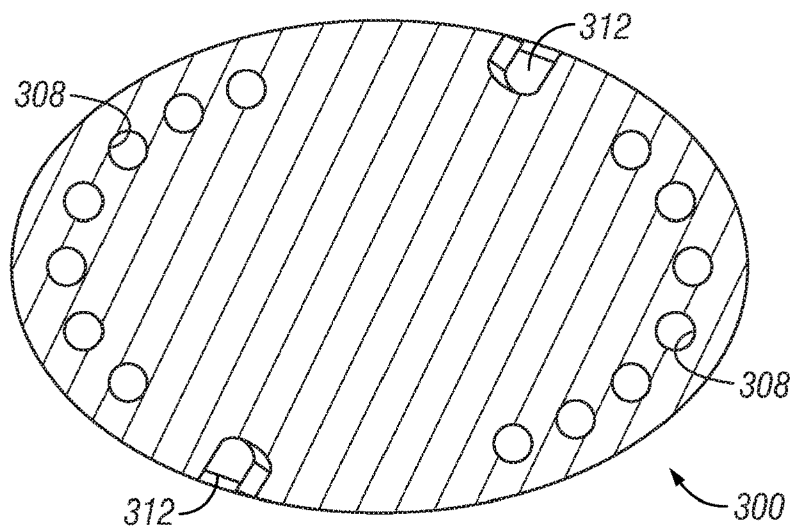
FIG. 4G illustrates a bottom cross-sectional view of an alternative embodiment of the mono-lead electrical lead protector of FIGS. 4A, 4B, 4C, 4D, 4E and 4F taken along the line B-B.

FIG. 4G illustrates a bottom view of an alternative embodiment of the mono-lead electrical lead protector of FIGS. 4A, 4B, 4C, 4D, 4E and 4F. Retaining grooves 312 are also illustrated.

Figure 4H:
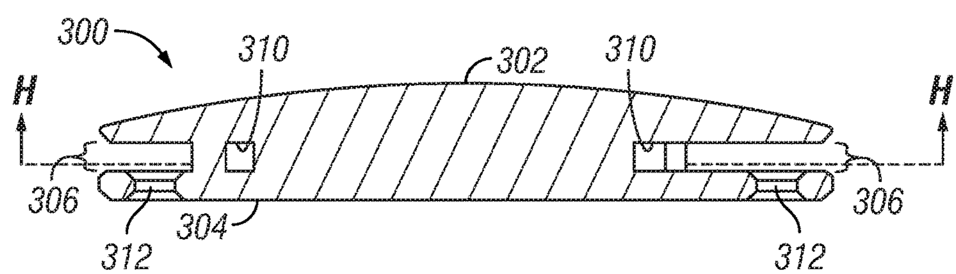
FIG. 4H illustrates a cross-sectional side view of an alternative embodiment of the mono-lead electrical protector of FIG. 4F, taken along the line F-F.
Figure 4I:
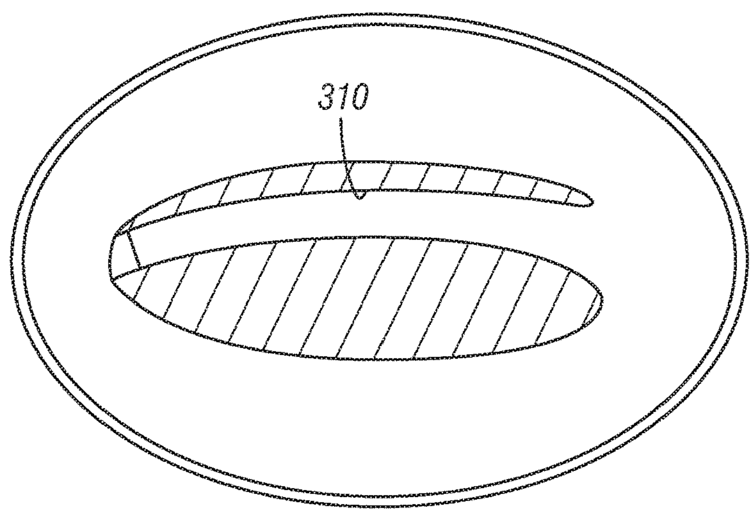
FIG. 4I illustrates a cross-section top view of an alternative embodiment of the mono-lead electrical protector of FIG. 4H, taken along the line H-H.

FIG. 4H illustrates a cross-sectional view of FIG. 4F and also illustrates a protective channel 310. Channel 310 receives the proximal end P of lead L and thereby stores and retains the proximal end P of lead L after implantation of lead L into the brain. As illustrated in FIGS. 4H and 4I, lead L is semi-rigid and generally retains its shape when inserted into protective channel 310. As discussed above, the diameter of lead L is on the order of 1.27 mm. The proximal end of lead L is inserted into protective channel 310. Preferably, channel 310, and all of lead protector 300, should be formed of a resilient deformable material that can receive and retain the proximal end of lead L. Preferably, channel 310 should be no more than 1.0 mm wide. In this way, lead L is removably retained within channel 310. This may be thought of as a pressure fit or an interference fit that occurs when the exterior surface of lead L and channel 310 are slightly plastically deformed. The result is that both parts elastically deform slightly creating a frictional force that removably retains lead L within channel 310. This may be thought of as holding lead L within channel 310. It has been found that if lead L is 1.27 mm that it will be removably retained when channel 310 is on the order of 1.0 mm. Protective channel 310 does not permanently retain lead L. Experiments with channel 310 indicate that an inner radius of 1.446 inches [3.672 centimeters] and an outer radius of 1.784 inches [4.531 centimeters] are preferred. Phrased differently, the inner and outer radiuses of channel 110 are not identical. This also means that the radiuses of curvature of the inner and outer radius are not the same. In other words, the inner wall has a radius on the order of about 1.446 inches [3.672 centimeters] and the outer wall has a radius of about 1.784 inches [4.531 centimeters].

As illustrated above in FIG. 3H-3J, Channel 310 retains the unimplanted end of lead L after lead P has been implanted into the patient's brain. Similarly, Channel 310 receives the proximal end P of lead L and thereby stores and removably retains the proximal end P of lead L after implantation of lead L into the brain FIGS. 4A, 4B, 4C, 4D, 4E, 4F, 4G, 4H and 4I illustrate the use of mono-lead electrical protector 300. Lead L is positioned in the brain. An adequate subgaleal pocket is formed. A skin incision of approximately three centimeters (1.2 inches) in length is made to bone depth. The skin incision is followed by a blunt dissection, typically using a curved hemostat with a digital dissection to provide a generous subgaleal pocket. Preferably, a sufficiently large subgaleal pocket, also referred to as a subgaleal space, is formed so that it is not necessary to force the mono-lead electrical protector 300 into the pocket. Mono-lead electrical protector 300 should preferably be oriented such that its bottom surface 304 is down. In other words, closer to the skull than top surface 302. The proximal end of lead L should be inserted into protective channel 310. Care should be taken to avoid bends, kinks or forcing of lead L during insertion of lead L into protective channel 310. Lead L may be wound around spool 306. Retaining groove 312 may then be used to hold lead L such it will not substantially unwind. Preferably, as seen in FIGS. 4A and 4H, retaining grooves 312 are located therethrough the bottom surface 304 of protector 300. Preferably, retaining grooves 312 are at a 45-degree angle and are slightly smaller than the width of lead L. For example, if lead L is 1.47 millimeters in diameter, grooves 312 should be 1.45 millimeters in across. For another example, if the lead L is 1.27 millimeters in diameter, grooves 312 should be 1.25 millimeters As discussed above, lead L is semi-rigid, groove 312 should be sized to retain lead L without substantially deforming it. Mono-lead electrical protector 300 is then implanted in the subgaleal space. Preferably, mono-lead electrical protector 300 is removably fixed to the pericranium using sutures that pass through one or more attachment loops 308. Closure of the wound over mono-lead electrical protector 300 helps insure against dehiscense. As discussed above, in many cases, a second procedure to retrieve and connect lead L to extension kit E and pulse generator G is employed. During this second procedure, a sufficient length of lead L is unwound to connect lead L to extension kit E and pulse generator G. As seen in FIG. 1C, pulse generator may be implanted in the shoulder region of the patient and extension kit E is implanted beneath the skin of the patient.

Figure 5A:
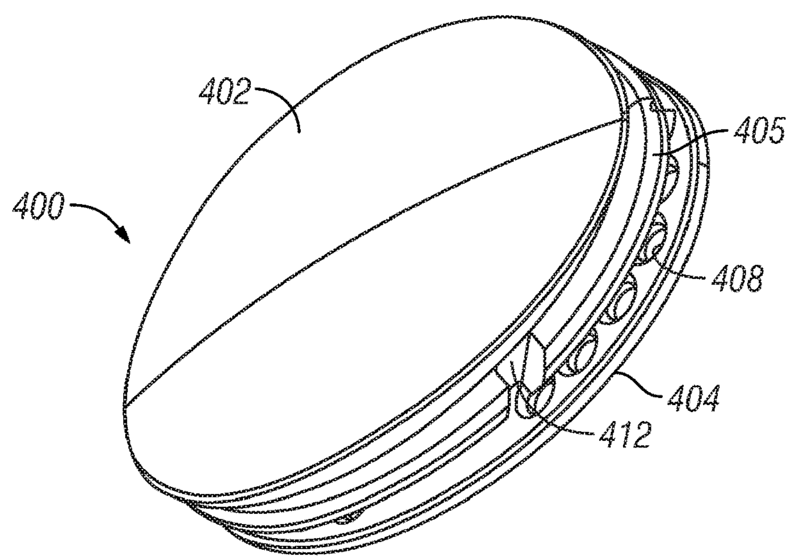
FIG. 5A illustrates a perspective view of an alternative embodiment of the bi-lead electrical lead protector.

FIG. 5A illustrates a perspective view of an alternative embodiment of the bi-lead electrical lead protector 400. Bi-lead electrical lead protector 400 further comprises top surface 402, bottom surface 404, spools 406, attachment loops 408, protective channels 410, and retaining grooves 412.

Figure 5B:
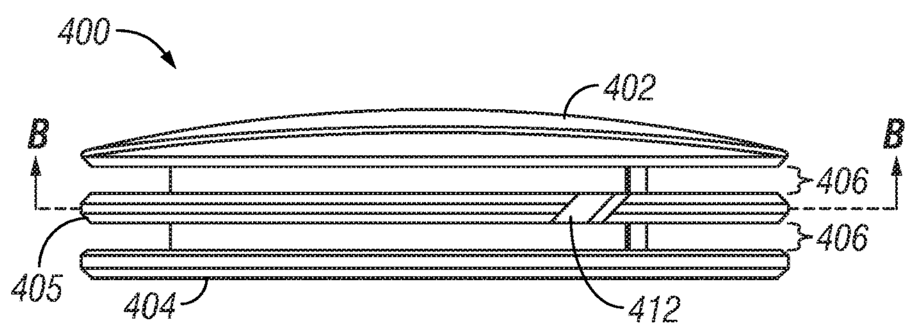
FIG. 5B illustrates a front plan view of the bi-lead electrical lead protector of FIG. 5A.

FIG. 5B illustrates a front view of the bi-lead electrical lead 400 protector of FIG. 5A.

Figure 5C:
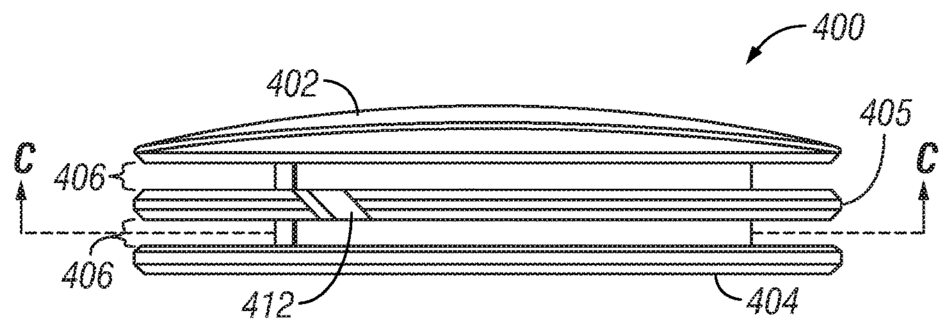
FIG. 5C illustrates a rear plan view of the bi-lead electrical lead protector of FIGS. 5A and 5B.

FIG. 5C illustrates a back view of the bi-lead electrical lead protector 400 of FIGS. 5A and 5B.

Figure 5D:
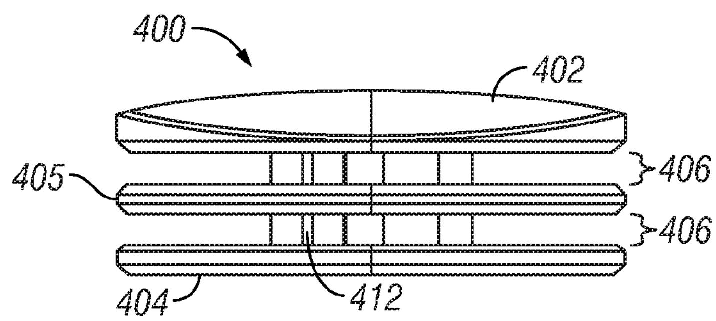
FIG. 5D illustrates a left side plan view of the bi-lead electrical lead protector of FIGS. 5A, 5B and 5C.

FIG. 5D illustrates a left side view of the bi-lead electrical lead protector 400 of FIGS. 5A, 5B and 5C.

Figure 5E:
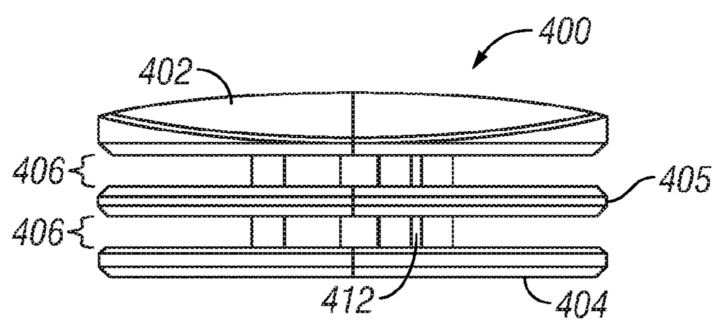
FIG. 5E illustrates a right side plan view of the bi-lead electrical lead protector of FIGS. 5A, 5B, C and 5D.

FIG. 5E illustrates a right side view of the bi-lead electrical lead protector 400 of FIGS. 5A, 5B, C and 5D.

Figure 5F:
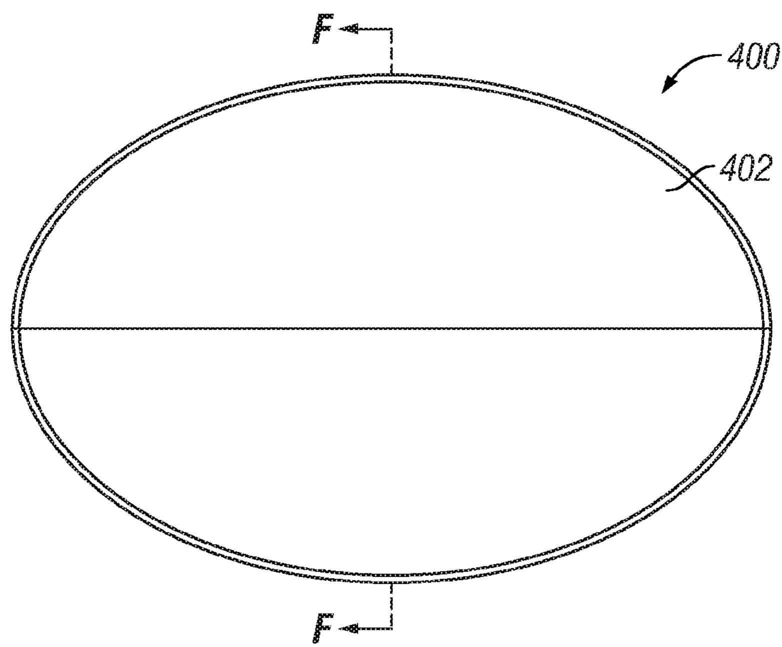
FIG. 5F illustrates a top plan view of the bi-lead electrical lead protector of FIGS. 5A, 5B, 5C, 5D and 5E.

FIG. 5F illustrates a top view of the bi-lead electrical lead protector 400 of FIGS. 5A, 5B, 5C, 5D and 5E.

Figure 5G:
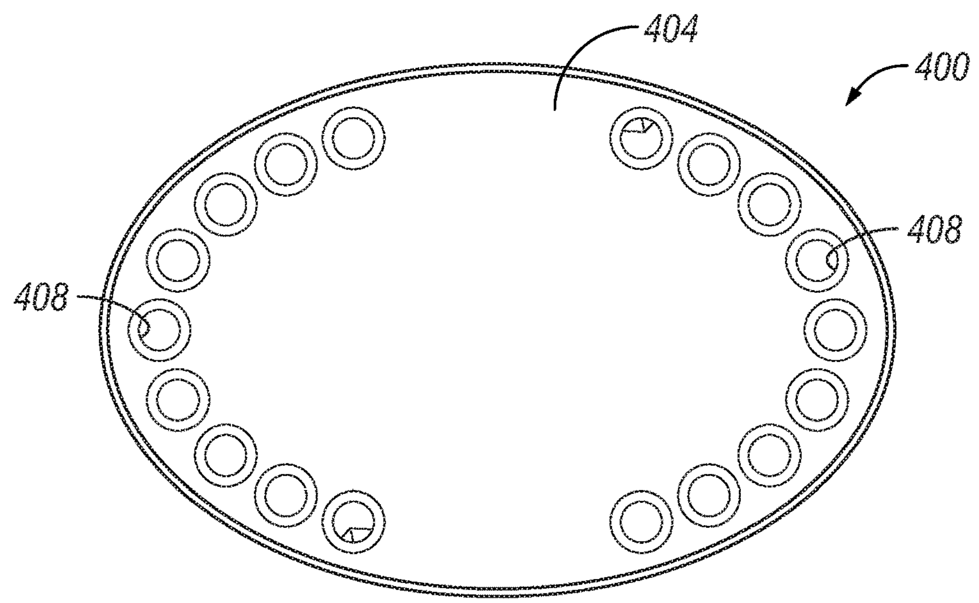
FIG. 5G illustrates a bottom plan view of the bi-lead electrical lead protector of FIGS. 5A, 5B, 5C, 5D, 5E and 5F.

FIG. 5G illustrates a bottom view of the bi-lead electrical lead protector 400 of FIGS. 5A, 5B, 5C, 5D, 5E and 5F. FIG. 5G illustrates attachment loops 408. Attachment loops 408 are employed for fixation of protector 400 to the pericranium.

Figure 5H:
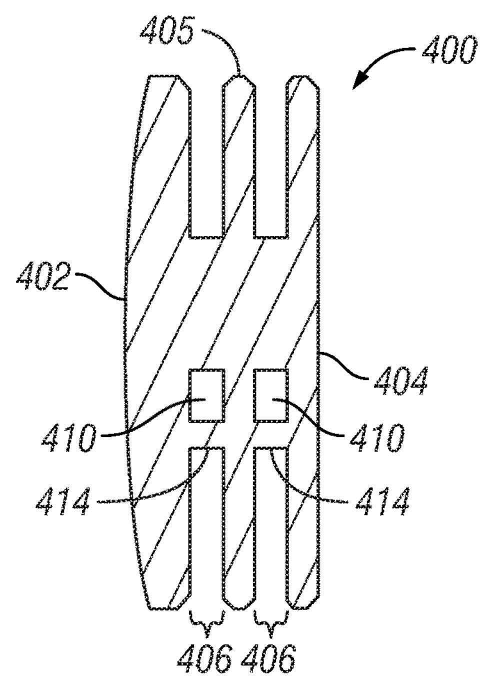
FIG. 5H illustrates a cross-section view of the bi-lead electrical protector of FIG. 5F, taken along the line F-F.

FIG. 5H illustrates a cross-sectional view of an embodiment of the bi-lead electrical protector 400 of FIG. 5F. FIG. 5H illustrates that bi-lead electrical protector 400 can retain two leads L. For example, a first lead L can be retained by first or upper protective channel 410 and a second lead L can be retained by a second or lower protective channel 410. Similarly, first lead L can be wound around first or upper spool 406 and second lead L can be wound around second or lower spool 406. If both leads L have substantially the same unimplanted length, each length may be wound around its respective spool concurrently. If leads L don't have substantially the same unimplanted length, each length may be wound around its respective spool separately.

Figure 5I:
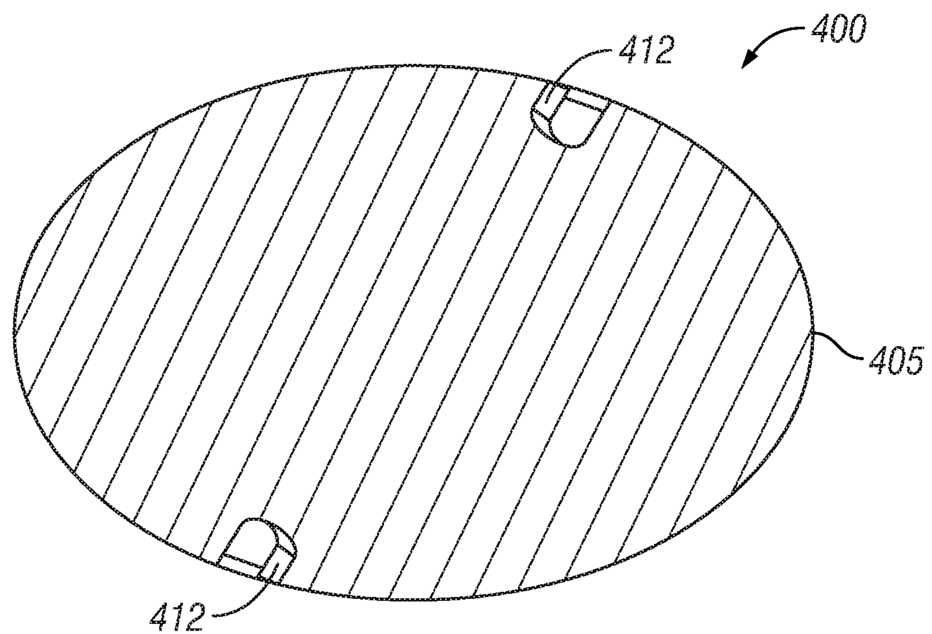
FIG. 5I illustrates a cross-sectional view of the bi-lead electrical protector of FIG. 5B, taken along the line B-B.

FIG. 5I illustrates a cross-sectional top view of an embodiment of the bi-lead electrical protector 400. FIG. 5I illustrates retaining grooves 412. Preferably, retaining grooves 412 are at a 45-degree angle and are slightly smaller than the width of lead L. For example, if lead L is 1.47 millimeters in diameter, grooves 412 should be 1.45 millimeters across. For another example, if lead L is 1.27 millimeters in diameter, grooves 412 should be 1.27 millimeters across. As discussed above, lead L is semi-rigid, groove 412 should be sized to retain lead L without substantially deforming it. It has been found that a pair of opposing retaining grooves 412 are preferable because retaining groove 412 is preferably sized with sufficient depth to retain two leads L. Phrased differently, a first lead L is positioned in retaining groove 412 and a second lead L is placed about first lead L. Second lead L helps to prevent first lead L from slipping out of retaining groove 412.

Figure 5J:
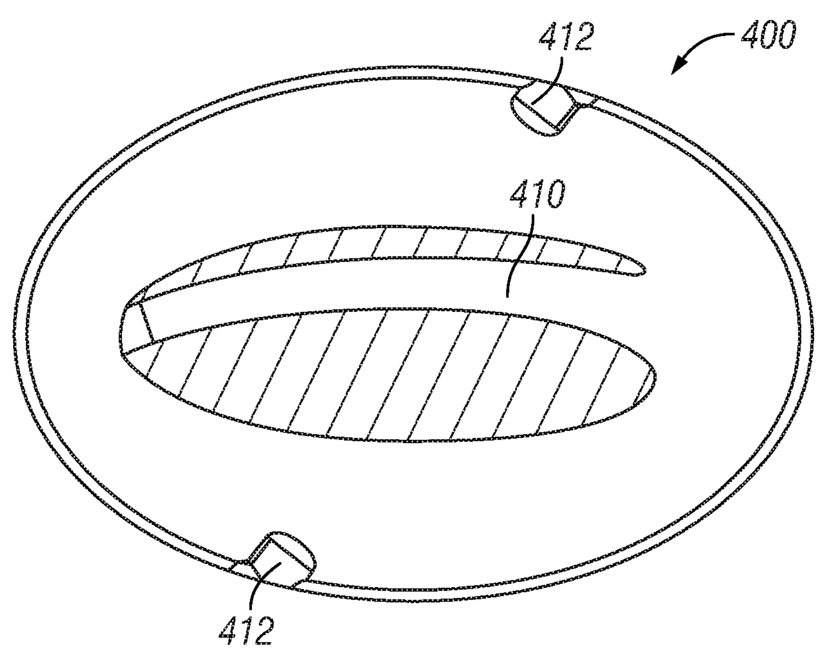
FIG. 5J illustrates a cross-sectional bottom view of embodiment of the bi-lead electrical protector of FIG. 5C, taken along the line C-C.

FIG. 5J illustrates a cross-sectional bottom view of embodiment of the bi-lead electrical protector 400 and illustrates second or lower protective channel 410 retaining lead L. Of course, a bi-lead electrical protector 400 could be used to retain a single lead L, but it is preferable to use mono-lead electrical protector 300 for that purpose.

As discussed above with respect to mono-lead electrical protector 300, bi-lead electrical protector 400 may be employed to protect two leads L. Correspondingly; two separate protectors could be used to protect one lead each.

Figure 6A:
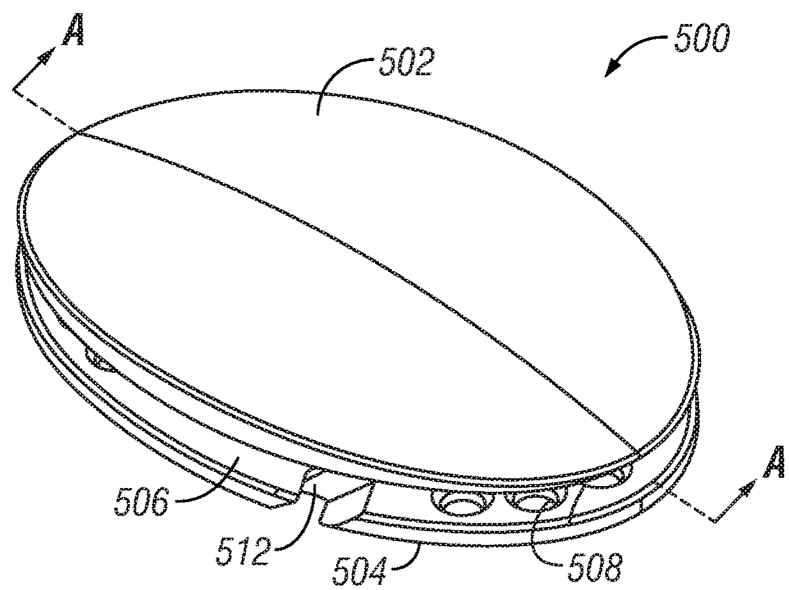
FIG. 6A illustrates a perspective view of an alternative embodiment of a mono-lead electrical lead protector.

FIG. 6A illustrates a perspective view of an alternative embodiment of a mono-lead electrical lead protector 500.

Figure 6B:
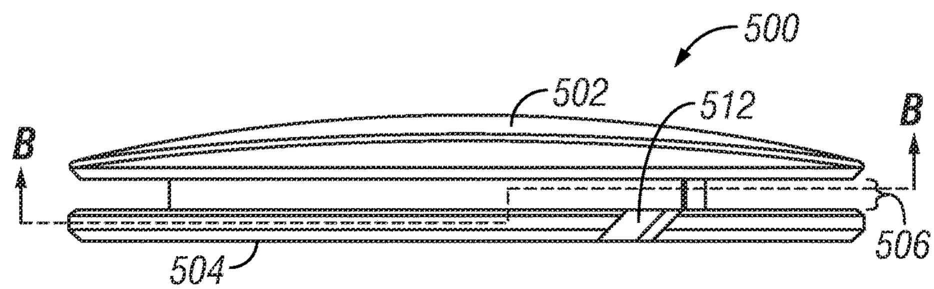
FIG. 6B illustrates a front plan view of the alternative embodiment of the mono-lead electrical lead protector of FIG. 6A.

FIG. 6B illustrates a front view of an embodiment the mono-lead electrical lead protector 500 of FIG. 6A. FIG. 6B also illustrates top surface 502, bottom surface 504, spool 506, attachment loops 508, protective channel 510, and retaining grooves 512.

Figure 6C:
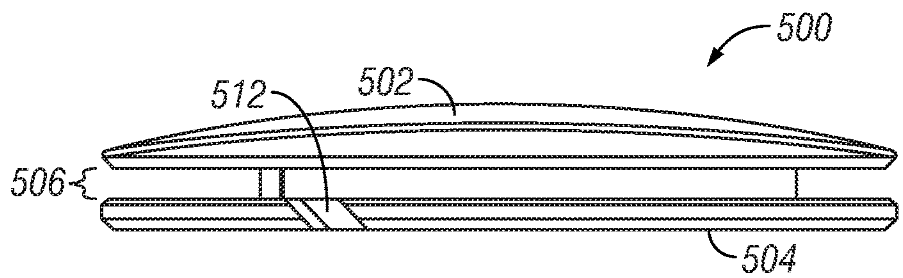
FIG. 6C illustrates a back plan view of the alternative embodiment of the mono-lead electrical lead protector of FIGS. 6A and 6B.

FIG. 6C illustrates a back view of an embodiment the mono-lead electrical lead protector 500 of FIGS. 6A and 6B.

Figure 6D:
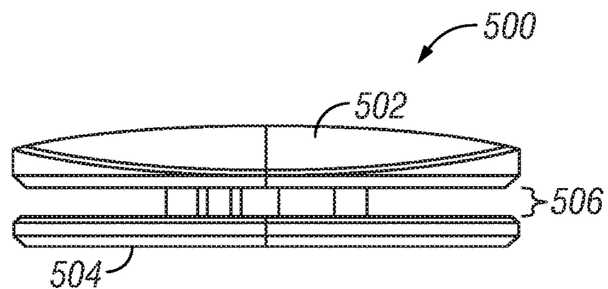
FIG. 6D illustrates a left side plan view of the alternative embodiment of the mono-lead electrical lead protector of FIGS. 6A, 6B and 6C.

FIG. 6D illustrates a left side view of an embodiment of the mono-lead electrical lead protector 500 of FIGS. 6A, 6B and 6C.

Figure 6E:
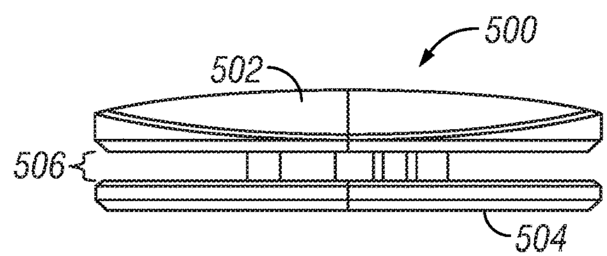
FIG. 6E illustrates a right side plan view the alternative embodiment of the mono-lead electrical lead protector of FIGS. 6A, 6B, 6C and 6D.

FIG. 6E illustrates a right side view of an embodiment of the mono-lead electrical lead protector 500 of FIGS. 6A, 6B, 6C and 6D.

Figure 6F:
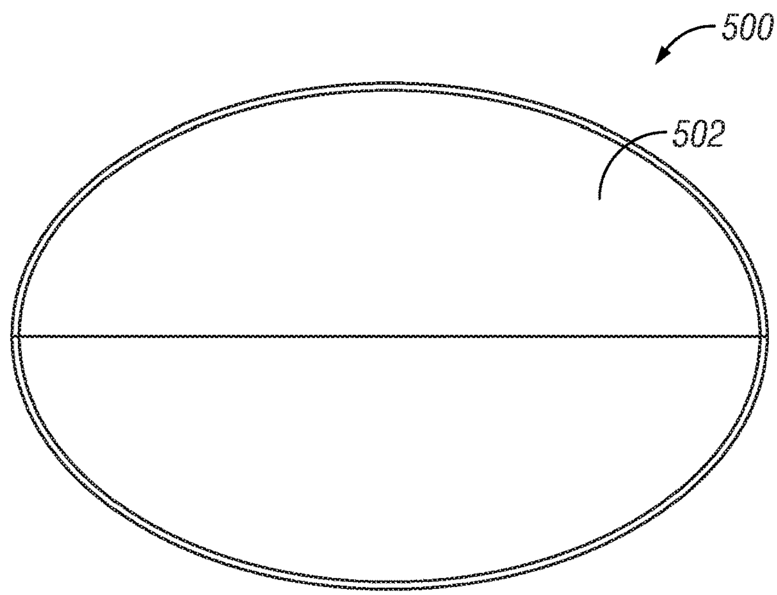
FIG. 6F illustrates a top plan view of the alternative embodiment of the mono-lead electrical lead protector of FIGS. 6A, 6B, 6C, 6D and 6E.

FIG. 6F illustrates a top view of an embodiment of the mono-lead electrical lead protector 500 of FIGS. 6A, 6B, 46, 6D and 6E.

Figure 6G:
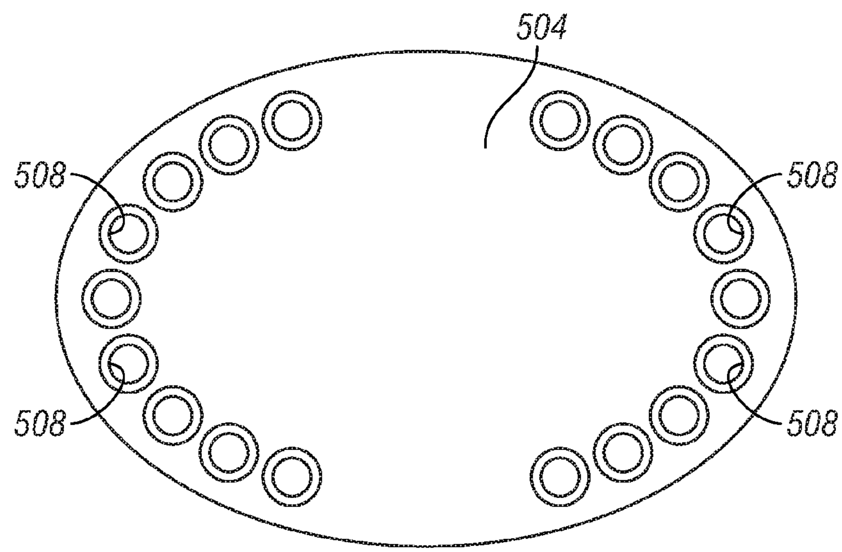
FIG. 6G illustrates a bottom plan view of the alternative embodiment of the mono-lead electrical lead protector of FIGS. 6A, 6B, 6C, 6D, 6E and 6F.

FIG. 6G illustrates a bottom view of an alternative embodiment of the mono-lead electrical lead protector of FIGS. 6A, 6B, 6C, 6D, 6E and 6F. While not illustrated, retaining grooves 612 could also be present.

Figure 6H:
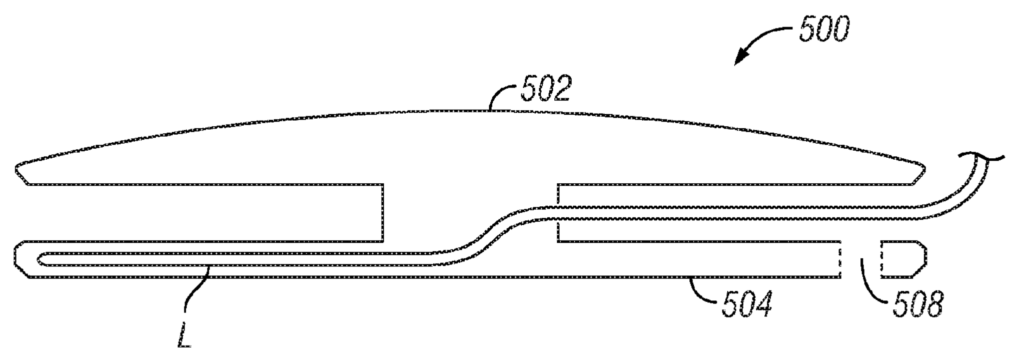
FIG. 6H illustrates a cross-sectional view the alternative embodiment of the mono-lead electrical protector taken along the line A-A.
Figure 6I:
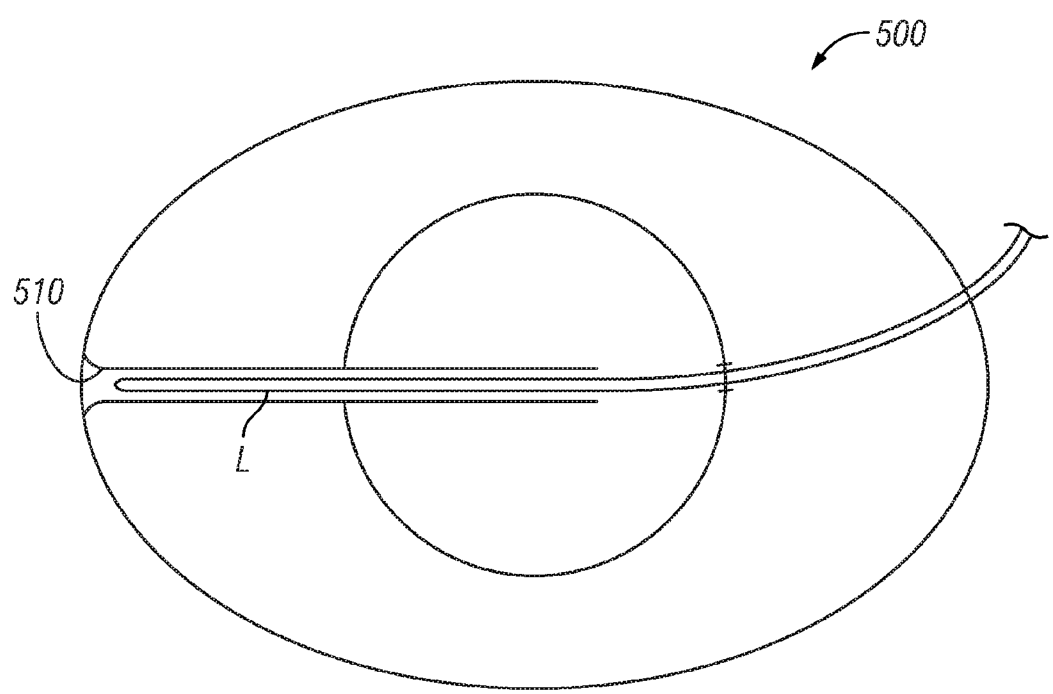
FIG. 6I illustrates a cross-sectional top view of the alternative embodiment of the mono-lead electrical protector of FIG. 6B taken along the line B-B and illustrating the lead being retained in the protective channel of the mono-lead electrical protector.

FIGS. 6H and 6I illustrate a protective channel 510. Channel 510 receives the proximal end P of lead L and thereby stores and removably retains the proximal end P of lead L after implantation of lead L into the brain. As illustrated in FIGS. 6H and 6I, lead L is semi-rigid and generally retains its shape when inserted into protective channel 510. As discussed above, the diameter of lead L is on the order of 1.27 mm. The proximal end of lead L is inserted into protective channel 510. Preferably, channel 510, and all of lead protector 500, should be formed of a resilient deformable material that can receive and retain the proximal end of lead L. Preferably; channel 510 should be no more than 1.0 mm wide. In this way, lead L is removably retained within channel 510. This may be thought of as a pressure fit or an interference fit that occurs when the exterior surface of lead L and channel 510 are slightly plastically deformed. The result is that both parts elastically deform slightly creating a frictional force that removably retains lead L within channel 510. This may be thought of as removably holding lead L within channel 510. It has been found that if lead L is 1.27 mm that it will be removably retained when channel 510 is on the order of 1.0 mm. Protective channel 510 does not permanently retain lead L, Experiments with channel 510 indicate that an inner radius of 1.446 inches [3.672 centimeters] and an outer radius of 1.784 inches [4.531 centimeters] are preferred. Phrased differently, the inner and outer radius of channel 510 are not identical. This also means that the radius of curvature of the inner and outer radius are not the same. In other words, the inner wall has a radius on the order of about 1.446 inches [3.672 centimeters] and the outer wall has a radius of about 1.784 inches [4.531 centimeters].

As illustrated above in FIG. 6H-6I, Channel 510 retains the unimplanted end of lead L after lead P has been implanted into the patient's brain. Similarly, channel 510 receives the proximal end P of lead L and thereby stores and removably retains the proximal end P of lead L after implantation of lead L into the brain.

Among the materials that SHIELDS 100, 200, 300, 400 and 500 may be formed from are polycarbonates. Preferably, lead protector 100, 200, 300, 400 is machined or molded from clear polycarbonate Lexan and is in compliance with ASTM F997 (Polycarbonate resin for Medical Applications). It is preferable that lead protects are translucent as this will more readily allow a user to insert lead L. Lexan® is a registered trademark of SABIC Industries for polycarbonates.

While the invention has been illustrated and described in detail in the drawings and description, the same is to be considered as an illustration and is not limited to the exact embodiments shown and described. All equivalents, changes and modifications that come within the spirit of the invention are also protected by the claims that are set forth below.

What is claimed is:

1. An implantable lead protector, for protecting a lead from damage, comprising:

a spool disposed between an upper surface and a lower surface;

a protective channel disposed at least partially therethrough and within the interior diameter of the spool;

whereby at least a portion of the lead can be slidably received into the protective channel and at least a portion of the lead may be wound around the spool and wherein the protective channel is in the same plane as the lead when the lead is wound around the spool.

2. The implantable lead protector of claim 1, further comprising:

a plurality of attachment loops.

3. The implantable lead protector of claim 2, wherein the attachment loops are symmetrically disposed therethrough the lower surface.

4. The implantable lead protector of claim 1, wherein at least one of the upper surface and the lower surface further comprise a plurality of retaining grooves.

5. The implantable lead protector of claim 4, wherein the retaining grooves are symmetrically disposed therethrough either the upper surface or the lower surface.

6. The implantable lead protector of claim 1, wherein at least a portion of the lead is retained within the protective channel due to an interference fit between the lead and the protective channel.

7. The implantable lead protector of claim 6, wherein at least a portion of the lead or the protective channel are plastically deformed due to the interference fit retaining the lead within the protective channel.

8. The implantable lead protector of claim 6, wherein the implantable lead protector is formed from polycarbonate resin.

9. The implantable lead protector of claim 6, wherein the implantable lead protector is translucent.

10. The implantable lead protector of claim 6, wherein the implantable lead protector is manufactured from machined or molded polycarbonate Lexan® in compliance with ASTM F997.

11. An implantable bi-lead protector for protecting leads from damage, comprising:

an intermediate surface disposed between an upper surface and a lower surface;

an upper spool disposed between the upper surface and the intermediate surface;

an lower spool disposed between the intermediate surface and the lower surface;

an upper protective channel disposed at least partially therethrough and within the interior diameter of the upper spool;

a lower protective channel disposed at least partially therethrough and within the interior diameter of the lower spool; and, whereby the upper protective channel can slidably receive one of the leads and the lower protective channel can slidably receive the other lead and at least a portion of the one of the leads may be wound around one spool and at least a portion of the other lead may be wound around the other spool and wherein each of the protective channels are in the same plane as the lead when the lead is wound around the respective spool.

12. The implantable bi-lead protector of claim 11, further comprising:

a plurality of attachment loops.

13. The implantable bi-lead protector of claim 12, wherein the attachment loops are symmetrically disposed therethrough the lower surface.

14. The implantable bi-lead protector of claim 11, wherein at least one of the upper surface, the intermediate surface, and the lower surface further comprise a plurality of retaining grooves.

15. The implantable bi-lead protector of claim 14, wherein the retaining grooves are symmetrically disposed therethrough either the upper surface, the lower surface or the intermediate surface.

16. The implantable bi-lead protector of claim 11, wherein at least a portion of the leads are retained within the protective channels due to an interference fit between the leads and the upper or lower protective channels.

17. The implantable bi-lead protector of claim 16, wherein at least a portion of the leads or the protective channels are plastically deformed due to the interference fit retaining the leads within the protective channels.

18. The implantable bi-lead protector of claim 16, wherein the implantable bi-lead protector is formed from polycarbonate resin.

19. The implantable bi-lead protector of claim 16, wherein the implantable lead protector is translucent.

20. The implantable bi-lead protector of claim 16, wherein the implantable lead protector is manufactured from machined or molded polycarbonate Lexan® in compliance with ASTM F997.

* * * * *